(12) United States Patent
Hatanaka

(10) Patent No.: US 9,895,502 B2
(45) Date of Patent: Feb. 20, 2018

(54) MEDICAL DEVICE AND METHOD FOR CONTROLLING SAME

(71) Applicant: TERUMO KABUSHIKI KAISHA, Tokyo (JP)

(72) Inventor: Youko Hatanaka, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 279 days.

(21) Appl. No.: 14/427,033

(22) PCT Filed: Sep. 26, 2012

(86) PCT No.: PCT/JP2012/006129
§ 371 (c)(1),
(2) Date: Mar. 10, 2015

(87) PCT Pub. No.: WO2014/049642
PCT Pub. Date: Apr. 3, 2014

(65) Prior Publication Data
US 2015/0238717 A1    Aug. 27, 2015

(51) Int. Cl.
*A61M 16/00* (2006.01)
*A61M 1/10* (2006.01)
(Continued)

(52) U.S. Cl.
CPC ...... *A61M 16/0051* (2013.01); *A61M 1/1086* (2013.01); *G05B 15/02* (2013.01);
(Continued)

(58) Field of Classification Search
CPC ............ A61M 16/0051; A61M 1/1086; A61M 2205/17; A61M 2205/18; A61M 2205/50; A61M 2205/583; G05B 15/02
See application file for complete search history.

(56) References Cited

U.S. PATENT DOCUMENTS 3,969,711 A * 7/1976 Ahntholz ............... G01R 19/14
340/651
6,868,309 B1   3/2005 Begelman
(Continued)

FOREIGN PATENT DOCUMENTS

JP        56035202        4/1981
JP         6327280        7/1988
(Continued)

OTHER PUBLICATIONS

EPO Office Action, Applicant—Terumo Kabushiki Kaisha, Application No. 12885320.7-1651, Ref. MUB15-1288EP, dated Jan. 27, 2017.
(Continued)

*Primary Examiner* — James Yang
(74) *Attorney, Agent, or Firm* — MacMillan, Sobanski and Todd, LLC

(57) ABSTRACT

A medical device has a first controller that has a control section responsible for sequence control of a device and is for controlling the medical device, a second controller that operates if a failure occurs in the first controller, and an alarm that makes a notification output based on exclusive OR between notification outputs of the first controller and the second controller. The second controller, after acquiring the notification output of the first controller, outputs its own notification output as it is if the notification output of the first controller is in an OFF state, or inverts its own notification output so as to output an inversion result if the notification output of the first controller is in an ON state.

6 Claims, 4 Drawing Sheets

(51) Int. Cl.
  *G05B 15/02* (2006.01)
  *G06F 19/00* (2018.01)
  *G08B 29/16* (2006.01)

(52) U.S. Cl.
  CPC ......... *G06F 19/3406* (2013.01); *G08B 29/16* (2013.01); *A61M 1/101* (2013.01); *A61M 1/1006* (2014.02); *A61M 2205/17* (2013.01); *A61M 2205/18* (2013.01); *A61M 2205/50* (2013.01); *A61M 2205/583* (2013.01)

(56) References Cited

U.S. PATENT DOCUMENTS

| | | | |
|---|---|---|---|
| 7,648,476 B2 | 1/2010 | Bock et al. | |
| 8,727,960 B2 | 5/2014 | Kanebako | |
| 2005/0242942 A1 | 11/2005 | Staats et al. | |
| 2008/0300572 A1* | 12/2008 | Rankers | A61B 5/14532 604/504 |
| 2010/0094221 A1* | 4/2010 | Spencer | A61M 5/1452 604/151 |

FOREIGN PATENT DOCUMENTS

| | | |
|---|---|---|
| JP | 03064131 | 3/1991 |
| JP | 03243195 | 10/1991 |
| JP | 04010798 | 1/1992 |
| JP | 04127730 | 4/1992 |
| JP | 05219032 | 8/1993 |
| JP | 06085714 | 3/1994 |
| JP | 2007014504 | 1/2007 |

OTHER PUBLICATIONS

Supplemental EPO Search Report, Application No. 12885277.9, dated Oct. 12, 2017.

* cited by examiner

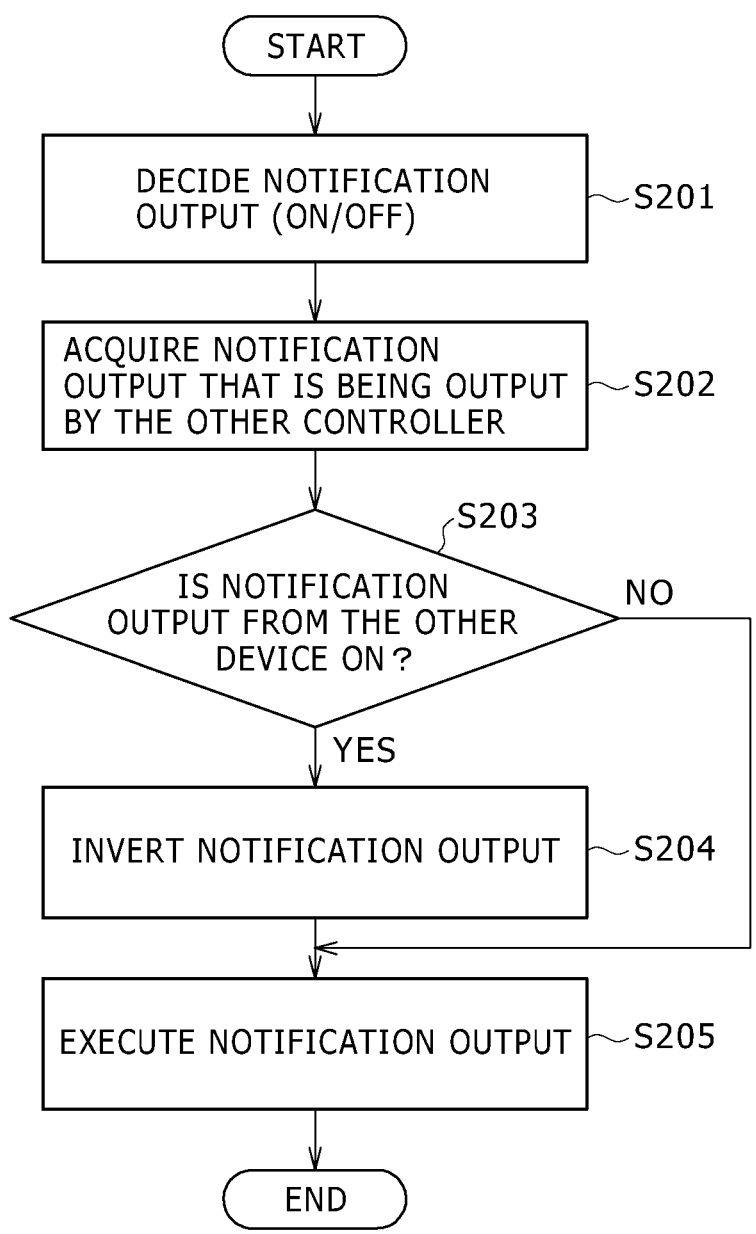

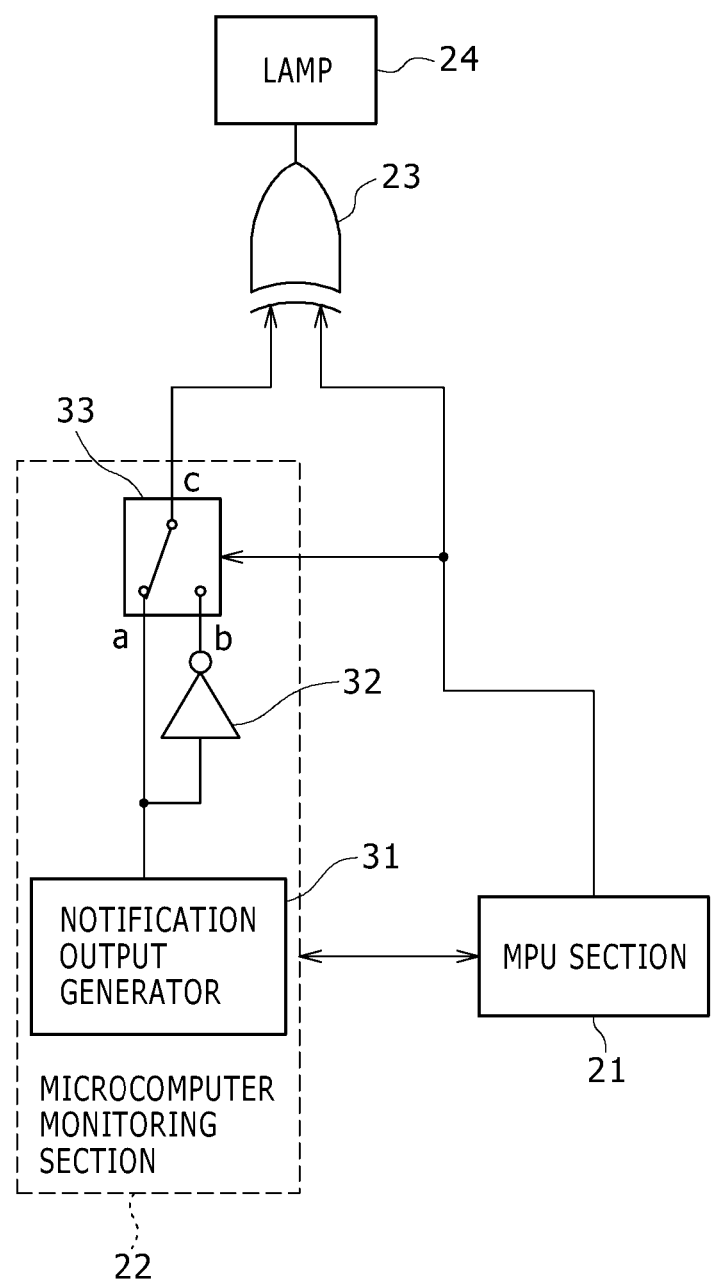

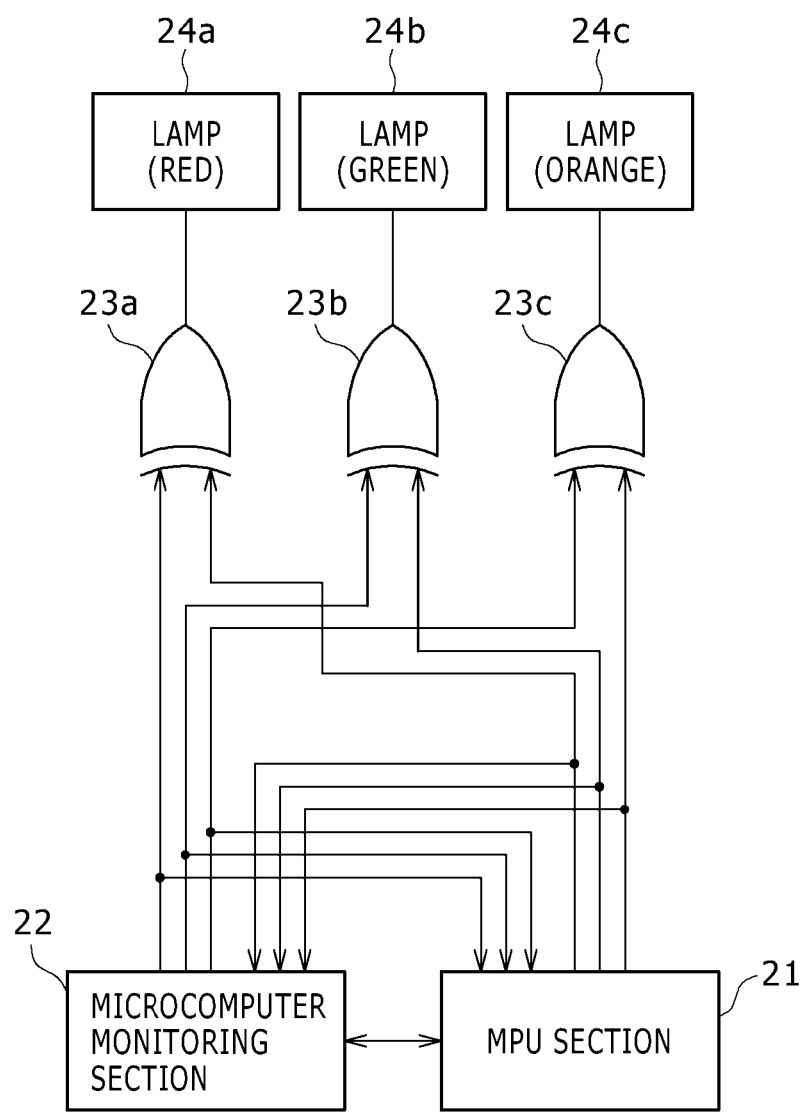

MEDICAL DEVICE AND METHOD FOR CONTROLLING SAME

TECHNICAL FIELD

The present invention relates to a medical device and a method for controlling the same.

BACKGROUND ART

In general, the complicated control of medical devices is implemented by a controller including a microcomputer. Among the medical devices are devices whose failure relates directly to the life of a patient, and extracorporeal circulation devices are cited as one of such devices. A representative one of the extracorporeal circulation devices is a cardiopulmonary assist device used during a cardiopulmonary procedure. This device includes a blood extracorporeal circulation circuit composed of oxygenator, centrifugal artificial heart (centrifugal pump), controller, and oxygen supply source (oxygen tank) (refer to Japanese Patent Laid-open No. 2007-14504). Since the cardiopulmonary assist device functions in place of the heart and lung of a patient, the device of high safety is being called for so that a situation in which it stops in the middle of an operation, for example, is avoided.

One method for ensuring the safety of such a medical device is to provide a control system for the medical device with a doubled structure having a main controller and a sub-controller. In this case, the sub-controller will continue the control even if the main controller stops due to some cause, and for this reason a safer system is achieved. One potential disadvantage is that the circuit scale becomes more complicated, with increases in the device size, the cost, and the power consumption.

According to another method, a configuration is employed in which a microcomputer monitoring device detects a stoppage or runaway of a main microcomputer and generates a warning when the stop or runaway of the microcomputer is detected. In this case, although complete backup of the system by doubling the controller is not available, a user will be able to rapidly restore the system by being immediately notified of a failure of the microcomputer.

SUMMARY OF INVENTION

It is desirable that an alarm such as a lamp and a buzzer for making various kinds of notification output during operation of a medical device be common whether doubling the controller is carried out or a microcomputer monitoring device like the above-described one is used. That is, it is desirable that the alarm circuits and notification devices be the same even whether the failure occurs in the main controller or the sub-controller. This is because providing separate alarms for each controller would lead to unnecessary increase in the number of alarms, potentially making the user confused.

To realize sharing of such an alarm, a configuration has been generally used in which the notification output of the main controller and that of the sub-controller or the microcomputer monitoring device are OR-connected and the OR-output thereof drives the alarm. However, in such a configuration, in a case where the main controller stops operating and its notification output is being held in an ON state, the notification output of the alarm would persist. During this time, it would be impossible for the user to identify the state of the alarm that may be generated by the sub-controller and the microcomputer monitoring device.

In particular, in the medical devices, arrangement of an alarm system (such as visual alarm and audio alarm) that notifies an equipment failure is required (IEC 60601-1 third edition as standards for medical equipment). When a lamp, for example, is used for warning, the color, the blink speed, and the duty cycle are prescribed in accordance with the contents and importance thereof. However, it might be impossible to realize such an alarm if the alarm is shared in the above-described way. For example, a constant illumination of the lamp may indicate a low priority alarm, a low flashing rate may indicate a medium priority alarm, and a faster flashing rate may indicate a higher priority alarm. If one controller generates a low priority alarm while the other controller generates a high priority alarm using a shared lamp, then only the low priority alarm becomes visible to the user because the lamp remains continuously illuminated.

The present invention is made in view of the above-described problem and an object thereof is to coordinate sharing of an alarm between a main controller and a backup device.

A medical device according to one aspect of the present invention for achieving the above-described object has the following configuration, for example. Specifically, a medical device includes a first controller that has a control section responsible for sequence control of a device and is for controlling the medical device, a second controller that operates if a failure occurs in the first controller, and notification means that makes a notification output based on exclusive OR between notification outputs of the first controller and the second controller, wherein the second controller, after acquiring the notification output of the first controller, outputs its own notification output unchanged if the notification output of the first controller is in an OFF state, or inverts its own notification output so as to output an inverted result if the notification output of the first controller is in an ON state. The logical result of taking the exclusive OR of the ON state of the first controller with the inverted state of the second controller is an output signal blinking at the higher rate intended by the second controller whenever the second controller generates a higher priority alarm.

According to the present invention, when a controller and a device for backup share an alarm, the device for backup is allowed to freely switch the state of the alarm with a simple configuration.

Other characteristics and advantages of the present invention will become apparent from the following description with reference to the accompanying drawings. It should be noted that the same or similar configuration is given the same reference numeral in the accompanying drawings.

BRIEF DESCRIPTION OF DRAWINGS

FIG. 2 is a flowchart for explaining notification output processing by a microcomputer monitoring section according to the embodiment.

FIG. 3 is a block diagram showing an example of a configuration to implement, using hardware, a notification output by the microcomputer monitoring section according to the embodiment.

FIG. 4 is a block diagram showing a state in which notification outputs according to the embodiment are made to correspond to a plurality of alarms.

DETAILED DESCRIPTION OF PREFERRED EMBODIMENTS

Figure 1:
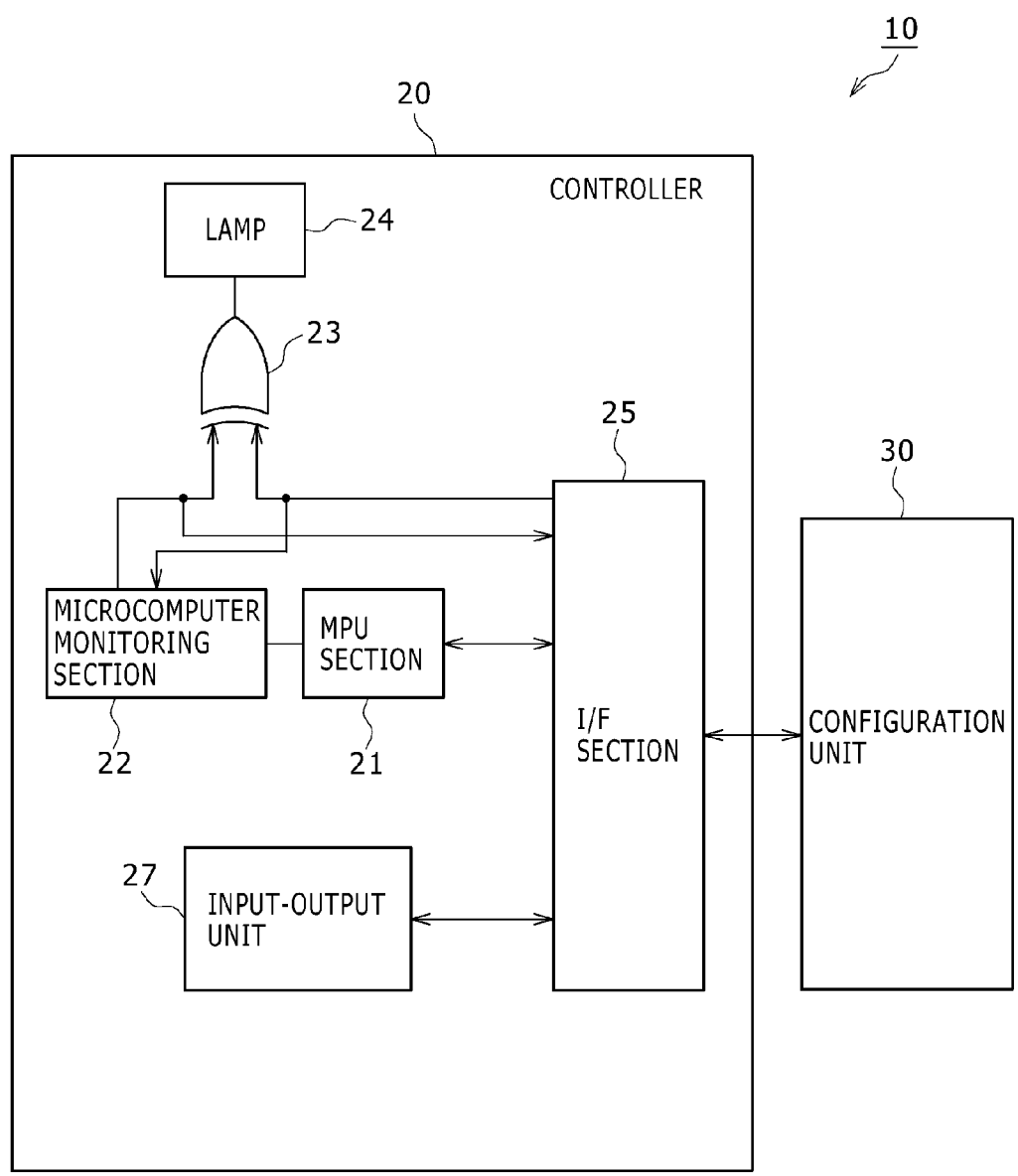
FIG. 1 is a block diagram showing the overall configuration of medical equipment according to an embodiment.

An embodiment of the present invention will be described in detail below with reference to the drawings.

FIG. 1 is a block diagram for explaining the concept of a medical device 10 according to the embodiment. An example of the medical device 10 is a life support system such as an extracorporeal circulation device (artificial cardiopulmonary device) and an artificial respirator. The medical device 10 has a controller 20 and a configuration unit 30 of the medical device controlled by the controller 20. In the controller 20, a microcomputer serving as a first controller that plays a role of a main controller includes an MPU section 21, an interface section 25, a ROM as a program memory and a RAM as a work memory, neither of which is shown. The MPU section 21 implements various kinds of control in the medical device 10 by executing a program stored in the ROM. In a case where an extracorporeal circulation device is applied as the medical device 10, for example, the configuration unit 30 would be a hardware configuration for extracorporeal circulation, such as a motor, a centrifugal pump, and an oxygenator. Although the microcomputer having the MPU section 21 is shown as a control section responsible for sequence control of the configuration unit 30 and a lamp 24 serving as an alarm section in the above, the configuration is not limited that, but a configuration in which an FPGA (Field Programmable Gate Array) or the like is used instead of the microcomputer may be employed as well.

A microcomputer monitoring section 22 functions as a second controller for monitoring the occurrence of a failure such as stop and runaway in the MPU section 21 and executing the necessary processing when detecting the occurrence of a failure. For example, at a time of a failure of the MPU section 21, the microcomputer monitoring section 22 provides a notification output for reporting the failure to an exclusive OR circuit section 23. The exclusive OR circuit section 23, after calculating the exclusive OR between notification outputs (ON and OFF) from the MPU section 21 and the microcomputer monitoring section 22, outputs a signal of the calculation result thereof to the lamp 24 as an alarm. It goes without saying that a sub-controller for doubling the controller may be used instead of the microcomputer monitoring section 22. Furthermore, the lamp 24 is used for notifying of the operation state and warning state of the device by the MPU section 21 and the microcomputer monitoring section 22. Moreover, although the lamp 24 is shown as one example of the alarm, the configuration is not limited thereto but a buzzer or the like that intermittently emits and stops a sound according to the notification output may be used.

An input-output of the MPU section 21 is connected to the interface section 25 and inputs-outputs of the configuration unit 30 of the medical device 10 are connected to the respective inputs-outputs of the MPU section 21. Another input-output unit 27 connected to the interface section 25 may provide a user interface such as a display section, an operation section, and so forth. In the present embodiment, the notification output from the MPU section 21 to the exclusive OR circuit section 23 is also output via the interface section 25. Moreover, the notification output from the MPU section 21 is also input to the microcomputer monitoring section 22. Similarly, the notification output from the microcomputer monitoring section 22 is also input to the MPU section 21 in addition to being input to the exclusive OR circuit section 23. The interface section 25 may be incorporated into the MPU section 21 as well.

At the time of the failure of the MPU section (i.e., main controller) 21, such as the stop and runaway of the MPU section 21, the microcomputer monitoring section 22 generates a notification output indicating the failure to the lamp 24 (lighting output to the lamp 24 in the present embodiment) and notifies a user of a warning. At this time, at the time of the runaway or the like, the MPU section 21 may keep the immediately previous notification output to the lamp 24 in some cases. If the MPU section 21 is in a state in which the notification output is OFF, the notification output (ON/OFF) from the microcomputer monitoring section 22 is reflected in an output signal of the exclusive OR circuit section 23. However, if the MPU section 21 keeps a state in which the notification output is ON, the notification output from the microcomputer monitoring section 22 is inverted by the exclusive OR circuit section 23. Therefore, the microcomputer monitoring section 22 checks the notification output of the MPU section 21. If the notification output of the MPU section 21 is ON, the microcomputer monitoring section 22 inverts its own notification output and then outputs it. In this way, a higher flashing rate of lamp 24 can be obtained since the second controller can generate a signal which extinguishes lamp 24 even though the notification output of MPU section 21 is ON.

FIG. 2 is a flowchart for explaining control of the notification output by the microcomputer monitoring section 22. If a failure such as the stop and runaway of the MPU section 21 occurs, the microcomputer monitoring section 22 detects this failure and enables itself to start the control and execute processing shown in FIG. 2. Note that the flowchart shown in FIG. 2 is repeatedly carried out after a failure of the MPU section 21 is detected and the control by the microcomputer monitoring section 22 is started.

First, in a step S201, the microcomputer monitoring section 22 decides whether its own notification output is to be ON or Off. The blink frequency and the duty cycle, in case that the runaway or stop of the MPU section 21 is notified, are configured in advance. The microcomputer monitoring section 22 switches the notification output (ON/OFF) in accordance with them.

In a step S202, the microcomputer monitoring section 22 acquires a notification output that is being output by the MPU section 21, which is the other controller. The microcomputer monitoring section 22, in a step S203, determines whether the notification output of the MPU section 21 acquired in the step S202 is in the ON state. If the notification output of the MPU section 21 is ON, the processing proceeds to a step S204, where the microcomputer monitoring section 22 inverts the warning output (ON/OFF) decided in the step S201. Then, in a step S205, the microcomputer monitoring section 22 outputs the inversion result to the exclusive OR circuit section 23 as a warning output. If the notification output of the MPU section 21 is not ON in the step S203, the processing directly proceeds to the step S205, where the microcomputer monitoring section 22 outputs the notification output decided in the step S201 as it is to the exclusive OR circuit section 23.

Although the inversion of the notification output is carried out by software in the above, the configuration is not limited thereto. For example, inversion of the notification output similar to the processing shown in FIG. 2 can be implemented also by a circuit configuration like the one shown in FIG. 3. In FIG. 3, description of the interface section 25 is omitted for the sake of simplification of the drawing. In FIG. 3, a notification output generator 31 executes processing like that explained in the step S201 to generate a notification output to be output by the microcomputer monitoring section 22. The generated notification output is connected to a terminal a of a selector 33 as it is. In addition, an output signal obtained by inversion of the generated notification output by an inverter 32 is connected to a terminal b of the selector 33. The notification output from the MPU section 21 is input to the selector 33. When the notification output from the MPU section 21 is OFF, the selector 33 connects the terminal a to a terminal c. When the notification output from the MPU section 21 is ON, the selector 33 connects the terminal b to the terminal c. Therefore, from the terminal c of the selector 33, the notification output generated by the notification output generator 31 is output as it is when the notification output of the MPU section 21 is in the OFF state; the inverted signal of the notification output generated by the notification output generator 31 is output when the notification output of the MPU section 21 is in the ON state. It is needless to say that it is possible to provide the inverter 32 and the selector 33 like the above-described ones also for the notification output of the MPU section 21.

As a result of the processing like the above-described one, whether the notification output state of the MPU section 21 is in the ON state or the OFF state, the microcomputer monitoring section 22 can freely turn on and off the lamp 24. Notifying in conformity with a blink form of an alarm (lamp) like the one prescribed in IEC 60601 as standards for medical equipment can be thereby implemented. In addition, as described above, it is also possible to use a buzzer as the alarm instead of the lamp 24. Thus, notifying in conformity with an alarm standard based on a sound like the one prescribed in IEC 60601 as standards for medical equipment can also be easily achieved.

In the above-described embodiment, the notification output of the microcomputer monitoring section 22 is loaded into the MPU section 21, and control for the notification output similar to that by the microcomputer monitoring section 22 is carried out also in the MPU section 21. Therefore, in a case where a situation occurs in which the microcomputer monitoring section 22 outputs some signal while the microcomputer monitoring section 22 is not in execution (i.e. while the MPU section 21 is in a normal operation), the correct notification output by the MPU section 21 would still be able to be reflected. However, as long as it is ensured that the microcomputer monitoring section 22 keeps the state in which its notification output is OFF while the MPU section 21 is in operation, the notification output of the microcomputer monitoring section 22 does not need to be loaded into the microcomputer side.

Although control of the notification output to one lamp or buzzer was explained in the above-described embodiment, the alarm may have a plurality of lamps or buzzers or they may exist in a mixed manner. In that case, a configuration is available in which the exclusive OR circuit section 23 is provided corresponding to each of the plural lamps or buzzers possessed by the alarm and a notification signal of each of the lamps or buzzers is independently processed. For example, as shown in FIG. 4, in a case where there are three lamps (lamps 24a, 24b, and 24c), a configuration would be available in which three exclusive OR circuit sections 23a, 23b, and 23c connected to the respective lamps are provided and notification output processing like that shown in FIG. 2 or a notification output circuit like that shown in FIG. 3 is independently provided for each lamp. Note that, also in FIG. 4, the interface section 25 is omitted for the sake of simplification of the drawing.

Furthermore, an alarm for which the contents of notification (notification state) are specified by a binary code may be used as well. For example, in FIG. 4, it is clear that application is possible also in case that a configuration in which the alarm treats a 3-bit binary code is adopted. In this case, for example, three exclusive OR circuit sections 23a, 23b, and 23c connected to the respective input bits of the alarm are provided and notification output processing like that shown in FIG. 2 or a notification output circuit like that shown in FIG. 3 is independently provided for each bit.

The present invention is not limited to the above-described embodiment and various changes and modifications are possible without departing from the spirit and scope of the present invention. Therefore, the following claims are attached in order to publicize the scope of the present invention.

The invention claimed is:

1. A medical device comprising:
a first controller that has a control section responsible for sequence control of the medical device, wherein the first controller includes a first monitoring section which generates a first notification signal having an ON state or an OFF state corresponding to detection of a failure in the first controller;
a second controller responsible for sequence control of the medical device if a failure occurs in the first controller, wherein the second controller includes a second monitoring section configured to detect a plurality of failures each having a respective priority, wherein the second controller generates a second notification signal in response to detecting one of the failures in the second controller, wherein the second notification signal has a flashing rate between an ON state and an OFF state identifying the respective priority, wherein one of the monitoring sections receives the notification signal from the other monitoring sections and inverts the second notification signal when the first notification signal is in an ON state; and
a shared alarm indicator that generates a perceptible output based on exclusive OR between the first and second notification signals.

2. The medical device according to claim 1, wherein the alarm indicator has a lamp that is turned on according to the exclusive OR between the first and second notification signals.

3. The medical device according to claim 1, wherein the alarm indicator has a sound emitter that emits a sound according to the exclusive OR between the first and second notification signals.

4. The medical device according to claim 1, wherein in order to perform notification using a plurality of alarms, the alarm indicator includes a plurality of elements each controlled independently corresponding to each of the plurality of alarms.

5. The medical device according to claim 1, wherein in order to perform notification according to a binary code, the alarm indicator includes a plurality of elements each controlled independently corresponding to each of a plurality of bits configuring a binary code input to the alarm.

6. A method of controlling a medical device, wherein the device comprises a first controller that has a control section responsible for sequence control of the medical device, a second controller responsible for sequence control of the medical device if a failure occurs in the first controller, and a shared warning indicator, wherein the method comprises the steps of:

the first controller generating a first notification signal corresponding to detection of a failure in the first controller;

the second controller generating a second notification signal corresponding to detection of one of a plurality of failures in the second controller each having a respective priority, and wherein the second notification signal has a flashing rate between an ON state and an OFF state which identifies the respective priority;

one of the controllers acquiring the notification signal of the other controller;

the one controller inverting the second notification signal when the first notification signal is in an ON state; and activating the warning indicator in response to an exclusive OR of the first and second notification signals, whereby the warning indicator maintains a flashing rate of the second notification signal without reduction by simultaneous generation of the first notification signal.

* * * * *